US009940815B1

(12) United States Patent
West

(10) Patent No.: US 9,940,815 B1
(45) Date of Patent: Apr. 10, 2018

(54) FLUID LEAK DETECTION ALARM SYSTEM

(71) Applicant: Kenneth D West, Bend, OR (US)

(72) Inventor: Kenneth D West, Bend, OR (US)

( * ) Notice: Subject to any disclaimer, the term of this patent is extended or adjusted under 35 U.S.C. 154(b) by 0 days.

(21) Appl. No.: 15/363,069

(22) Filed: Nov. 29, 2016

Related U.S. Application Data

(60) Provisional application No. 62/370,161, filed on Aug. 2, 2016.

(51) Int. Cl.
*A61F 13/42* (2006.01)
*G08B 21/20* (2006.01)

(52) U.S. Cl.
CPC .................................... *G08B 21/20* (2013.01)

(58) Field of Classification Search
CPC combination set(s) only.
See application file for complete search history.

(56) References Cited

U.S. PATENT DOCUMENTS 7,834,234 B2 * 11/2010 Roe ......................... A61F 13/42 604/361
9,140,658 B1 * 9/2015 Anklesaria ............. G01N 27/12

* cited by examiner

*Primary Examiner* — Brian Zimmerman
*Assistant Examiner* — Cal Eustaquio
(74) *Attorney, Agent, or Firm* — Mark S Hubert

(57) ABSTRACT

A system having a user configurable and sizeable planar sensor pad having electrical circuits thereon, adjacent to a trough or groove formed in the sensor pad. These circuits are energized upon the application of a conductive fluid into the trough and once activated initiates a wireless communication device to transmit an alarm to a mobile device of the user, such as a smart phone, alerting the user of the detected fluid leak. The device may be self contained, operating on its own DC power source and may not require the use of a computer, a WI-Fi signal, or the internet.

19 Claims, 6 Drawing Sheets

FLUID LEAK DETECTION ALARM SYSTEM

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

PREVIOUS APPLICATIONS

This patent incorporates by reference in its entirety herein and claims priority from US provisional patent 26/527680 titled “Leak Detection System” filed Aug. 2, 2016.

FIELD

The present disclosure relates, in general, to detection of fluid leaks, and more particularly to remote alarm notification technology as applied to household leak detection.

BACKGROUND

Water leaks have been an ongoing and common problem associated with hot water heaters, washing machines, sinks, and various other water-dependent appliances, widespread in homes, townhouses, apartments, mobile homes, and offices. Water leaks have accompanied such water employing or generating appliances for as long as such modern appliances and indoor plumbing have been installed in buildings. Frequently the leaks result a considerable amount of structural damage to the building, as and their contents.

Because such water leaks can develop slowly, frequently they are not discovered until significant damage has already occurred, or upon the substantial accumulation of water has developed.

Consequently, it would be advantageous for building occupants to have an early-warning alarm system for detecting such common and frequently slowly-developing water leaks before costly repairs become necessary.

While leak detection systems have been previously developed, most such systems are not easily installed and monitored and either employ too small sensors which may or may not come into contact with fluid due to their placement under the large footprint.

A few pad sensors are known that have attempted to remedy this problem of lack of detection by providing a larger footprint with a plurality of sensors upon it. However, such conventional pad sensors are not adjustable in overall size due to wiring for sensors and other factors, so they are provided in fixed sizes, which may not be suitable for certain configurations. If they are available in various sizes, it increases the retailer's inventory and also drives up manufacturing costs.

Because of this lack of adjustability, users must seek sensing pads and components which are of a sufficient size to cover the footprint area of concern, and adequately sense a small and slow leak. Even then, such users will frequently find they are unable to find a proper sized sensing pad resulting in a choice between one which is too small to adequately sense the entire footprint area, or too large to properly position in a smaller footprint area underneath the associated appliance.

As a further problem, the prior art sensors utilize local audible alarms and operate on electrical power, which may or may not be available nearby and which can become unplugged or unpowered in the event of a power outage.

As such, there is a long felt need for a leak detection system which employs a sensing component configured to sense the smallest of fluid leaks in the largest possible footprint area of the appliance or plumbing of concern and be able to wirelessly transmit a self powered, alarm signal to the owner's smart phone, tablet or computer. An improved leak detection alarm system is provided by the embodiments set forth below. This new invention utilizes and combines known and new technologies in a unique and novel configuration to overcome the aforementioned problems and accomplish this.

BRIEF SUMMARY

In accordance with various embodiments, an improved leak detection alarm system is provided.

In one aspect, a self contained fluid leak detection and directable alarm system able to be physically configured by trimming to cover areas of different geometrical shapes, is provided.

In another aspect, a self contained fluid leak detection alarm system that is able to detect minute amounts of leaking fluid and that wirelessly notifies a party able to make corrective actions, is provided.

In yet another aspect, a fluid leak detection alarm system that is operated by an integrated, independent power source is provided.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION

Figure 1:
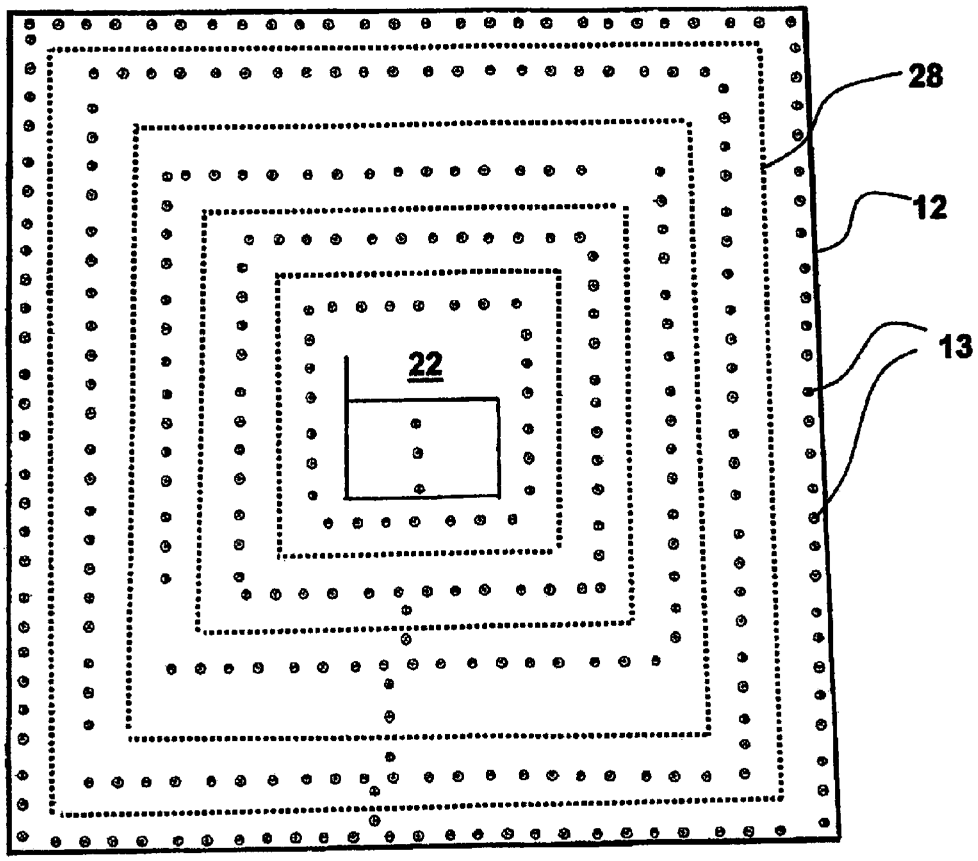
FIG. 1 is a top view of the first layer of the alarm pad.
Figure 2:
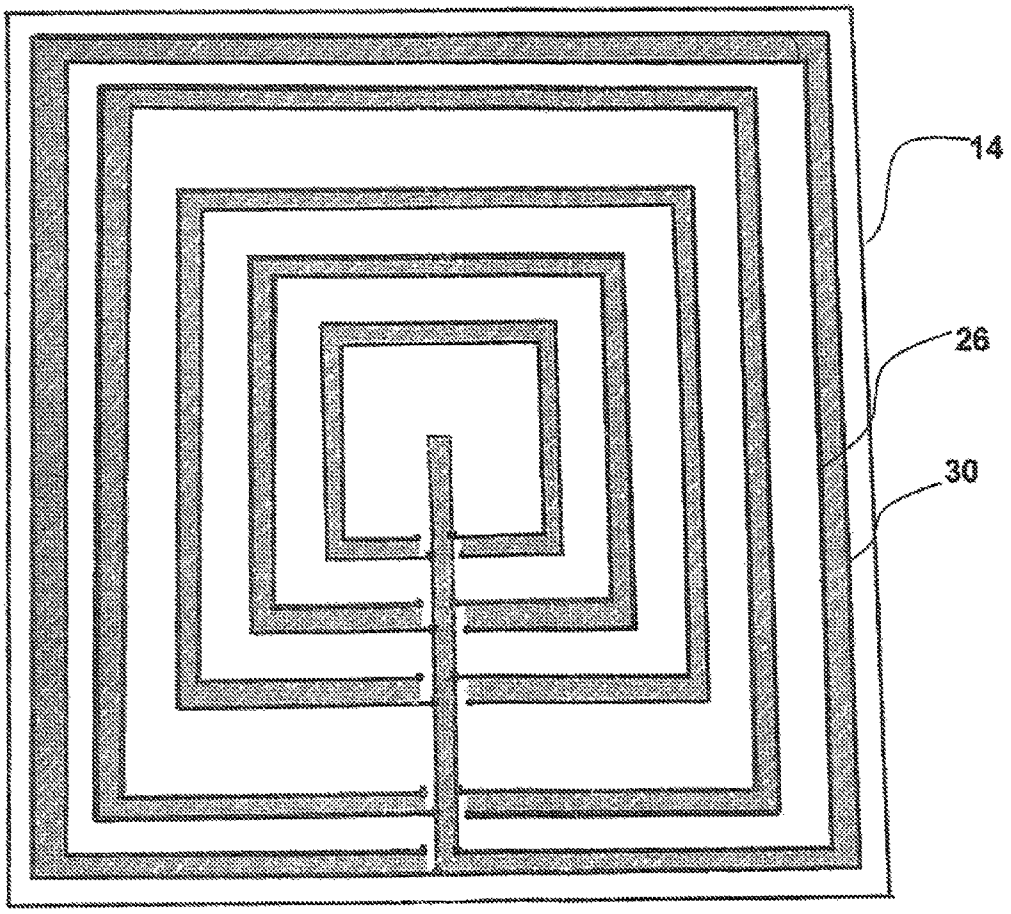
FIG. 2 is a top view of the second (fabric) layer of the preferred embodiment alarm pad.

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The term "microprocessor" as used herein refers to a microprocessor processing device and its necessary operational components such as memory microchips. A microprocessor is a device that is capable of performing the algorithmic instructions stored in its non volatile memory. Generally these microprocessors are housed or mounted on a planar substrate such as a printed circuit board that provides the support and electrical connectivity between the other components in operable communication with the microprocessor, such as wireless transmitters. In general, embodiments can employ as a processor, any device or combination of devices, that can operate to execute instructions to perform functions as described herein. Merely by way of example, and without limitation, any microprocessor can be used as a processor, including without limitation one or more complex instruction set computing (CISC) microprocessors, such as the single core and multi-core processors available from Intel Corporation™ and others, such as Intel's X86 platform, including, e.g., the Pentium™, Core™, and Xeon™ lines of processors. Additionally and/or alternatively, reduced instruction set computing (RISC) microprocessors, such as the Raspberry Pi™ line of processors, processors employing chip designs by ARM Holdings™, and others can be used in many embodiments. In further embodiments, a processor might be a microcontroller, embedded processor, embedded system, system on a chip (SoC) or the like.

As used herein the term "transmitter" refers to a piece of electronic equipment capable of either transmitting or both transmitting and receiving electronic signals. Bluetooth transmitters use a wireless technology standard for exchanging data over short distances (using short-wavelength UHF radio waves in the ISM band from 2.4 to 2.485 GHz[4]) from fixed and mobile devices, and building personal area networks (PANs). WiFi transmitters allow electronic devices to connect to a wireless LAN (WLAN) network, mainly using the 2.4 gigahertz (12 cm) UHF and 5 gigahertz (6 cm) SHF ISM radio bands. General Packet Radio Service (GRPS) transmitters is a packet-based wireless communication service that promises data rates from 56 up to 114 Kbps and continuous connection to the Internet for mobile phone and computer users. GPRS is based on Global System for Mobile (GSM) communication and complements existing services such circuit-switched cellular phone connections and the Short Message Service (SMS).

The terms "pad, sensing pad and alarm pad" as used herein, refer to the planar housing, the means for moisture signal generation and optionally the signal translation means if it is integrated thereon or therein the pad.

As used herein the terms "device, and leak detection alarm system" refer to the operational assembly of the grouped mechanical, electronic, electric and computer structural components that make the disclosed invention operable.

The term "means for moisture signal generation" as used herein, refers to a system capable of generating an electric impulse or electronic signal in response to the contact of a fluid upon at least one of its components. Generally this contact changes electrical resistivity within the means or completes an electric circuit within the means, either of which result in an initiation signal which is detectable by electrical/electronic/computer equipment (signal translation means) which can act on this detection and subsequent initiation signal to generate or initiate the generation of an alarm signal. The "means for moisture signal generation" includes such systems as disclosed with respect to the embodiments described herein as well as functional or operational equivalents. The term as used herein including the claims, is to be interpreted according to 35 USC 112 ¶ 6.

The term "signal translation means" as used herein, refers to electrical/electronic/computer equipment capable of receiving an initiation signal and generating an alarm signal. Generally and herein, it will be a microprocessor (microprocessor system) capable of performing the algorithmic instructions stored in its non volatile memory. It may vary in its level of complexity.

With respect to the following detailed description, before explaining at least one preferred embodiment of the herein disclosed fluid leak detection and alarm system in detail, it is to be understood that the invention is not limited in its application to the details of construction and to the arrangement of the components in the following description or illustrated in the drawings. The invention herein described is capable of other embodiments and of being practiced and carried out in various ways, obvious to those skilled in the art. Also, it is to be understood that the phraseology and terminology employed herein are for the purpose of description and should not be regarded as limiting.

The device herein disclosed and described provides a solution to the shortcomings in prior art of fluid leak detection alarm systems sensing below appliances, plumbing fixtures and the like.

Looking at FIGS. 1-3 and 5 the preferred embodiment of the present invention can best be seen. The leak detection alarm system is made of three components; a generally planar frangible, waterproof sensing pad 16, a means for moisture signal generation housed therein the pad 16, and a signal translation means 20 also housed therein or thereon the pad 16.

The pad 16 has a top layer 12 (FIG. 1) which when mated (preferably bonded) with the bottom layer 14 (FIG. 2), forms the generally planar sensing pad 16 herein. The top layer 12 is positioned so as to be adjacent and in contact with bottom layer 14 across a trench or dado area there between. The top layer and bottom layer may be formed of any material suitable to hold a respective series of rings forming circuits such as a conductive material such as copper or the like as herein described. Such might be woven, non woven, laminated, or other planar materials.

This sensing pad 16 is configured to communicate an electronic initiation signal generated by the means for moisture signal generation, over operatively engaged wires 18 (visible only in the alternate embodiment of FIG. 4) to a signal translation means 20. The signal translation means 20 generates and transmits an alarm signal into response to its receipt of the initiation signal once a leak is detected. The alarm signal is acted upon by a remote device in wireless communication with the signal translation means 20 so as to generate a text message, an email message or a recorded phone message to the users smart phone, personal computing device or tablet. The signal translation means 20 may optionally enable audible alarm 21.

Figure 5:
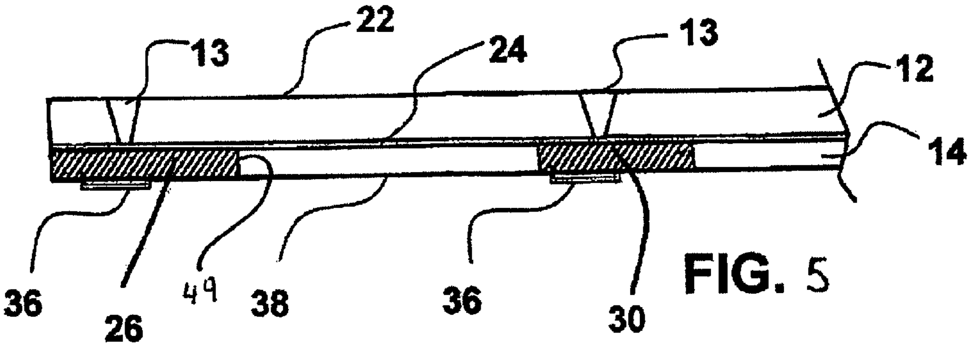
FIG. 5 is a side cross sectional view of the preferred embodiment alarm pad formed by the engagement of the top surface and bottom surface of FIGS. 1 and 2, showing respective conductive areas on each which are aligned to mate across a gap between the top and bottom surfaces.
Figure 7:
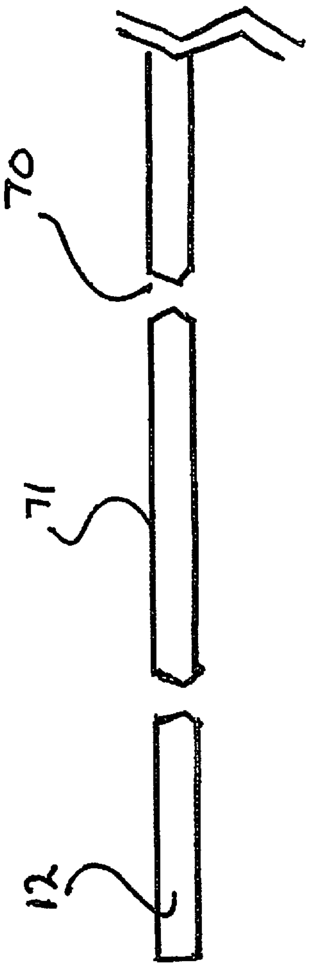
FIG. 7 is a side cross sectional view of the first layer of the alarm pad.

The top layer 12 has a plurality of apertures 13 therein, (preferably tapered into a funnel or venturi shape) configured to communicate fluid to a trench or dado 49 formed between the top layer 12 and bottom layer 14 of the pad 16. On the alarm pad fluid will collect and pool on the top face of the top layer, which is waterproof. Fluid that contacts any aperture is drawn into that aperture 13 and will close a circuit or alter the electrical resistivity of the means for moisture signal generation described herein so as send an initiation signal to the signal translation means 20. The venture aperture 70 (FIG. 7) has the added advantage of drawing in more fluid from the waterproof top face of the pad than the funnel aperture. As depicted, the apertures 13 are positioned to follow a pattern of concentric rings which are formed by the parallel running first conductive surface 26 and second conductive surface 30 (FIG. 5). Surface tension aids in drawing the leaked fluid down the apertures.

The top layer 12 is as noted, engaged to a position immediately adjacent the bottom layer 14. The bottom layer 14 has a first and a second conductive surface area formed therein. The first conductive surface area 26 and second conductive surface area 30 may communicate through the bottom layer 14 such as being formed by conductive thread sewn into and communicating between a first side and second side of the bottom layer 14. These first and second conductive surface areas engaged upon the bottom surface are preferably formed as a second series of parallel rings. Each of the first and second conductive surface areas are sized and positioned upon the bottom layer in a fashion complementary to the size and positioning of the first conductive surface area running parallel thereto. The first and second conductive surface areas run in parallel around the bottom surface thereby forming a series of concentric rings where the larger of the rings surround one or more smaller rings.

In this fashion, when the bottom layer is connected with the top layer, the first conductive surface area formed by the first series of rings is a mirrored parallel configuration of the second conductive surface area formed by the second series of rings formed of conductive material.

Figure 3:
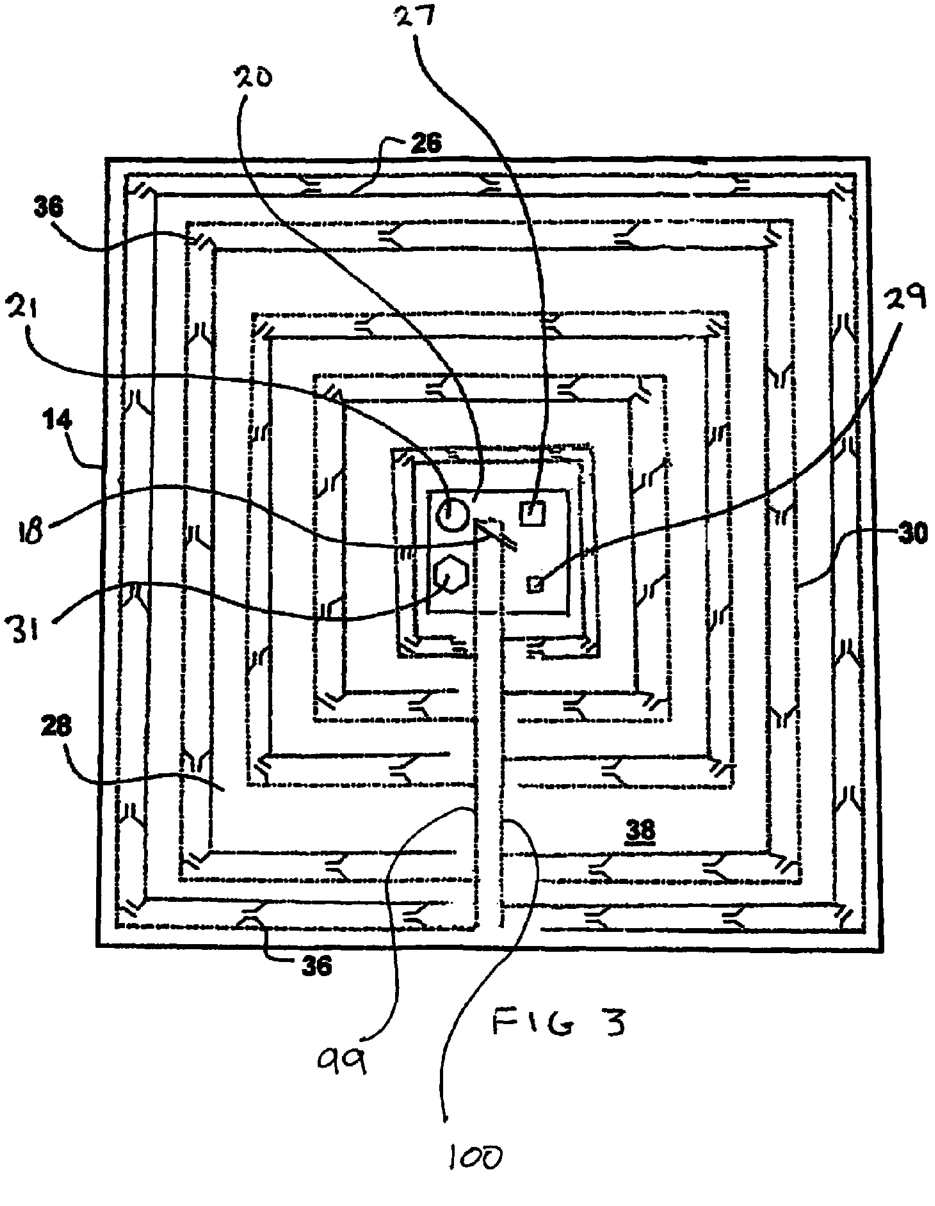
FIG. 3 is a top view of the bottom surface of the second layer of the preferred embodiment alarm pad.

Looking at FIG. it can be seen that the first conductive surface 26 shown as a first line, parallels the second conductive surface shown as the abutting or substantially parallel second line, both of which are positioned upon the second or bottom layer 14 in a configuration, as shown, to match a pattern formed by the apertures 13. In this fashion, water communicated through the apertures 13 is communicated to the area of the bottom layer 14 which is in-between the first conductive surface 26 and second conductive surface 30 in a fashion most likely to cause a closure and formation of a circuit which will generate a signal sent to the signal translation means 20. As also can be seen, on the second or bottom layer 14, the parallel first conductive surface 26 and second conductive surface 30 are positioned to form a series of concentric rings on the second or bottom layer 14. An interconnecting section of parallel lines of conductive material electrically connects each portion of the first conductive surface 26 and respective second conductive surface 30 forming each of the concentric series of rings. The interconnecting section of parallel lines of conductive material has a first conductive line 99 and a second conductive line 100, said first conducive line 99 operative connected to said first conductive surface 26 and said second conductive line 100 operatively connected to said second conductive surface 30 of each of said concentric rings in said series of concentric rings. (FIG. 3)

Thus, electric communication is provided through an interconnecting section of conductive material, extending from the respective first and second conductive surface layers in the largest of the formed rings, to a respective distal end of the interconnecting section, positioned within an interior area of a respective smallest of the series of rings formed by the parallel running first conductive surface area and second conductive surface area. The formed rings of first and second conductive surface areas will still electrically contact the respective first and second conductive surface areas of other formed rings of conductive material. In this fashion, when the bottom layer is connected with the top layer, the first conductive surface area formed by the first series of rings is a mirrored parallel configuration of the second conductive surface area formed by the second series of rings formed of conductive material.

Wires 18 extend from the signal translation means 20 to the first interconnecting section connecting all of the respective first and second conductive surface areas running adjacent and parallel in the formed series of rings on the lower surface. These wires communicate the electric signal based on resistance in the formed circuits of each of the first and second conductive surface areas. Any fluid which becomes positioned between and contacting any of the first and second conductive surface areas forming any of the rings, will cause a change in the electric signal since the resistance will change from the fluid interposed between the two series of rings on the first layer and second layer of the pad.

During use, should a leak develop, fluid contacting and communicating through the apertures 13 of the top layer 12 will become positioned in-between the abutting first and second conductive surfaces on the bottom layer 14. Even a small amount of fluid so positioned, will cause a connection between both the first and second conductive surfaces and cause an electrical change by forming a resistive connection therebetween which will be communicated to the signal translation means 20 which will thereafter issue and alarm that fluid is present in the monitored area.

At least one of the parallel running first conductive surface area and second conductive surface area are powered, and in a wired communication with the signal translation means 20 so as to provide an electric initiation signal from the electric current run through the wires and the first conductive surface area and second conductive surface area forming the series of rings on the lower surface of the pad.

The electric initiation signal will be static at a determined level, when the pad 16 and both surfaces are dry. This electric signal changes when fluid contacting the top layer of the pad communicates through one or a plurality of apertures in the top layer, and into the trough in-between the abutting series of rings formed of the first and second surface layers of conductive material on the bottom layer of the pad. Even a very small amount of fluid, passing through an aperture of the top layer, to become positioned in-between and in contact with the first conductive surface layer and an adjacent parallel second conductive surface layer, will change the electronic signal communicated to the signal translation means 20.

The exterior of the first layer and/or second layer which when engaged form the pad, may be marked with indicia for employment by the user to cut the pad to smaller sizes. Even when so cut to smaller sizes, the formed rings of first and second conductive surface areas will still electrically contact the respective first and second conductive surface areas of other formed rings of conductive material, with the largest ring in the series being that which was inside the perimeter edge cut from the formed pad by a user. In this fashion, the pad may be adjusted for the size of the desired footprint of fluid sensing by the user, and it will still be fully functional with all of the formed first conductive surface areas and second conductive surface areas running parallel to form rings, in operative electrical contact.

As also noted, indicia 28 such as that shown on the exterior surface 22 of the top layer 12 of the pad 16 may be provided on the formed pad 16, allowing the user to trim the pad 16 to a smaller footprint. This indicia 28 may be printed or embossed to provide guide lines or the conductive material such as conductive thread sewn through the second or bottom layer 14 can provide such guide lines to allow trimming of the pad 16 to a smaller footprint by removal of the largest ring section, while still maintaining the connections of the first conductive surface and second conductive surface throughout the remaining formed rings. Even when so trimmed, the first series of rings formed by the parallel running first conductive surface 26 and second conductive surface 30, will still be connected by any fluid therebetween and the electric signal will still be generated should fluid such as water enter though an aperture 13.

Finally, in order to sense fluid which might be present on a support surface underneath the second or bottom layer 14, optionally a series of connectors 36 can be provided which are exposed to the support surface on the lower side of the second or bottom layer 14. The connectors 36 are in communication with either a respective first conductive surface 26 or second conductive surface 30 formed into or on the bottom layer 14, such that fluid communicated in-between two connectors 36 which are electrically connected with respective first and second conductive surfaces, will cause the signal translation means 20 to sense an initiation signal and act thereon so as to alert the user or people within audible range of the device.

The signal translation means 20 is a printed circuit board operationally housing a microprocessor 23, an operably connected battery 25, an audible alarm 21, a wireless WiFi transmitter 27, a wireless Bluetooth transmitter 29, and a general packet radio system (GPRS) transmitter 31. Upon receipt of an initiation signal, the signal translation means may initiate the powering of a localized audible alarm 21 (preferably a localized attached piezoelectric transducer); or generate an alarm text message and send the alarm text message in one or all of three different ways: via a radio signal to a third party's subscription service through the general packet radio system transmitter (GPRS); via a wireless signal through the WiFi transceiver 27 to a local area network (LAN); or via the Bluetooth transceiver 29 (or an operational equivalent type of transmitter/transceiver) to a paired Bluetooth device. The signal translation means 20 can be discovered and put into operational communication with any paired Bluetooth device or device on the LAN that is running the companion software application designed for communication with the signal translation means 20. Such software has been developed and is well known in the industry.

The LAN connected devices or Bluetooth connected devices generally will be a smart cell phone or portable computing devices (PCD). The companion software application is downloaded into the smart cell phone's or PCD's operating system. This companion software does two things. First, it has a discovery mechanism, that if the phone or the PCD is connected to the LAN via wireless WiFi connection, it will find any signal translation means 20 connected to the same LAN, and thereafter, communication between these two LAN connected devices will be established following internet protocol, as is well known in the industry. The signal translation means 20 upon receipt of an initiation signal sends an alarm signal notification via WiFi to the LAN which may be interpreted and presented in a visual textual or audible format on the LAN connected devices.

Second, the smart cell phone or PCD with the software application will discover any Bluetooth signal sent by the Bluetooth transceiver 29, and after Bluetooth pairing has been completed, connecting these two devices for communication using established Bluetooth protocol as is well known in the industry. The signal translation means 20 upon receipt of an initiation signal sends an alarm signal notification via Bluetooth (near field communication) which may be interpreted and presented in a visual textual or audible format on the Bluetooth connected devices.

There is also another way that the signal translation means may communicate a leak to the user via their smart cell phone. Here the signal translation means connects to the LAN via WiFi and sends an electronic message to the user's mobile device carrier via the local area network, directing the mobile device carrier to send an alarm text message to the user's mobile device via the mobile device's carrier system when an alarm is generated.

In a fourth way, the signal translation means 20 upon receipt of an initiation signal, sends a radio frequency message which is picked up by a third party's GPRS subscription service. This is a monthly fee provided service that receives the alarm text message directly via the GPRS which integrates it with the cell phone carrier's system so as to allow the alarm text message to be received on the user's cell phone.

Figure 4:
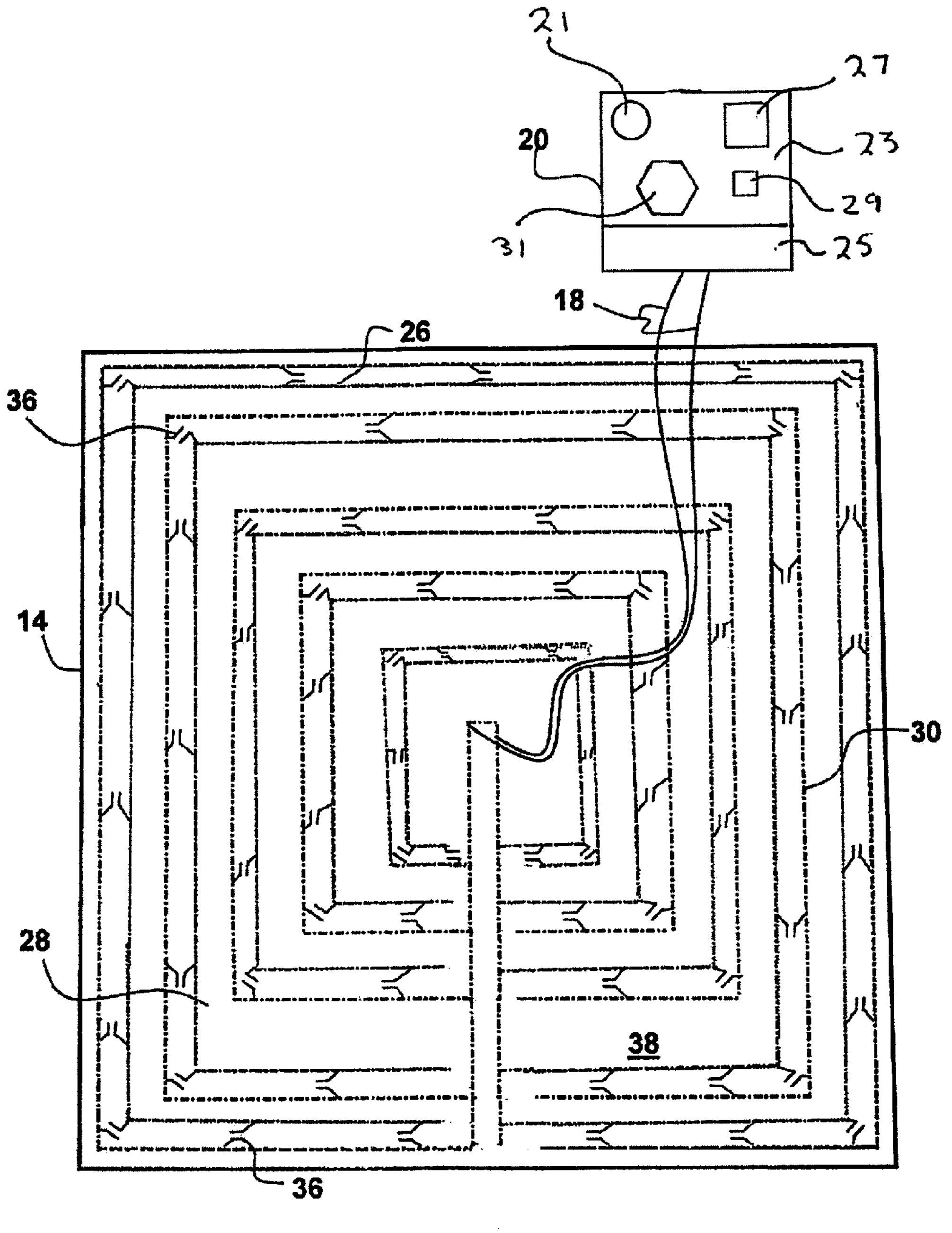
FIG. 4 is a top view of the bottom surface of the second layer of the alternate embodiment alarm pad.

Looking at FIG. 4 an alternate embodiment pad utilizing the identical means for moisture signal generation as the preferred embodiment can best be seen. This alternate embodiment has the identical components as the preferred embodiment but the signal translation means 20 is not physically affixed to or incorporated into the physical structure of the pad. Rather, it is hard wired to the means for moisture signal generation but enclosed in its own housing separable from the planar pad 16. The signal translation means 20 may then be located in a nearby location capable of broadcasting WiFi, Bluetooth or GPRS signals with a longer transmission range.

As an option not illustrated, in the preferred or alternate embodiment pads an AC power source may be operationally connected with or without a backup battery. Such conversions are well known in the industry and by one skilled in the art. However, this defeats much of the intended purpose of the device, which is to provide a simplified, stand-alone fluid leak detection alarm system.

Figure 6:
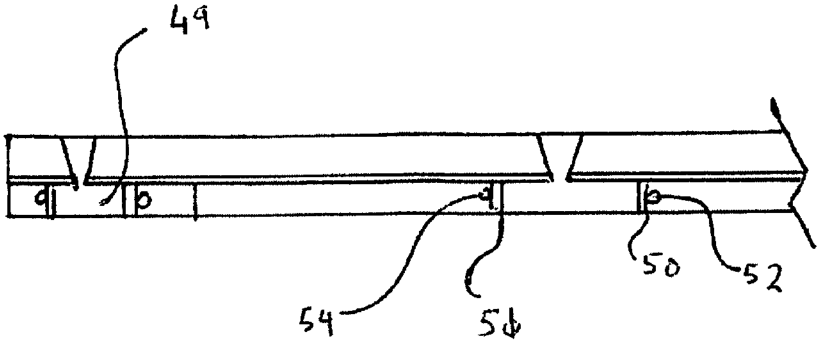
FIG. 6 is a side cross sectional view of the alternate embodiment alarm pad.

FIG. 6 illustrates an alternate means for moisture signal generation. This may be substituted in the previously discussed primary or alternate embodiments. Such different electronic designs and mechanical layouts of means for moisture signal generation are well known in the industry and by one skilled in the art. Here, a first 50 and second series of adjacent but spaced electrical conductors 51 are placed within the trough 49. Each electrical conductor 50 or 51 in the first or second series is connected to the other conductors in that first or second series by wires 52 and 54. When a fluid enters the trough 49 it spans between the first and second conductors (at least one of which is electrically powered) and completes an electrical circuit that constitutes the initiating signal that reaches the signal translation means 20. These, again form a concentric series of rings on the lower surface of the pad as described above.

Since this device is designed to operate on an independent power source, preferably a long life DC battery such as a Lithium Polymer will be used. Since there is but a trickle current to the microprocessor, the battery should have a multi year use before replacement is needed. The microprocessor may not be constantly powered but rather, a repeating, timed, circuit test pulse may be employed to further extend the life of the battery. These circuit test pulses are well known in the electronics industry.

This invention has other applications, potentially, and one skilled in the art could discover these. The explication of the features of this invention does not limit the claims of this application; other applications developed by those skilled in the art will be included in this invention.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture, but instead can be implemented on any suitable hardware, firmware, and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

The invention claimed is:

1. A moisture detection alarm pad comprising:

a generally planar pad, having a top face made of a waterproof material;

a means for moisture signal generation disposed within said pad as a series of cuttingly removeable individual concentric rings, said rings made of a first conductive surface area positioned parallel to a second conductive surface area;

an interconnecting section of parallel lines of conductive material operatively connected to said first conductive surface area and to said second conductive surface area of each concentric ring in said series of concentric rings, wherein each concentric ring may be cut and removed from said series of concentric rings and a remaining series of concentric rings will remain operatively connected to said interconnecting section of parallel lines to remain functional as an operative electric alarm circuit;

a signal translation means affixed to said pad and operably connected to receive an initiation signal from said means for moisture signal generation and in response to reception of said initiation signal, outputs a wireless alarm signal.

2. The moisture detection alarm system of claim 1 wherein said interconnecting section of parallel lines of conductive material has a first conductive line 99 and a second conductive line 100, said first conducive line 99 operative connected to said first conductive surface 26 and said second conductive line 100 operatively connected to said second conductive surface 30 of each of said concentric rings in said series of concentric rings.

3. The moisture detection alarm system of claim 1 wherein said signal translation means comprises:

a microprocessor;

a battery;

at least one wireless signal transmitter;

wherein said microprocessor, said battery and said transmitter are housed on a printed circuit board.

4. The moisture detection alarm system of claim 3 wherein said wireless signal transmitter is selected from the group of wireless signal transmitters including WiFi transmitters, Bluetooth transmitters and GRPS transmitters.

5. The moisture detection alarm system of claim 3 wherein said signal translation means further comprises an audible alarm device.

6. The moisture detection alarm system of claim 3 wherein said pad has a top layer with a series of apertures therethrough, said top layer affixed to a bottom layer, said bottom layer having a series of concentric troughs formed therein, where said troughs reside between said first and second conductive surfaces of said means for moisture signal generation which reside therein said bottom layer.

7. The moisture detection alarm system of claim 6 wherein said first and said second conductive surfaces provide an electric signal to said signal translation means when a fluid enters said concentric troughs and contacts said conductive surfaces.

8. The moisture detection pad of claim 6 wherein said apertures are tapered inward from top to bottom and are aligned in a series or concentric rings residing above said concentric troughs.

9. The moisture detection pad of claim 6 wherein said apertures are venture apertures and are aligned in a series or concentric rings residing above said concentric troughs.

10. The moisture detection pad of claim 7 wherein said bottom layer has a system of embedded conductive wires therethrough in electrical communication with said first and second conductive surfaces of said means for moisture signal generation and said signal translation means.

11. A moisture detection alarm pad comprising:

a generally planar pad having a top face that is made of a waterproof material;

a means for moisture signal generation disposed within said pad in a series of concentric rings;

a signal translation means operably connected to receive an initiation signal from said means for moisture signal generation and in response to reception of said initiation signal, outputs a wireless alarm signal.

12. The moisture detection alarm system of claim 10 wherein said signal translation means comprises:

a microprocessor;

a battery;

at least one wireless signal transmitter;

wherein said microprocessor, said battery and said transmitter are housed on a printed circuit board.

13. The moisture detection alarm system of claim 12 wherein said wireless signal transmitter is selected from the group of wireless signal transmitters including WiFi transmitters, Bluetooth transmitters and GRPS transmitters.

14. The moisture detection alarm system of claim 12 wherein said signal translation means further comprises an audible alarm device.

15. The moisture detection alarm system of claim 12 wherein said pad has a top layer with a series of apertures therethrough affixed to a bottom layer with a series of concentric troughs formed therein that a first and a second conductive surface of said means for moisture signal generation resides therein.

16. The moisture detection alarm system of claim 14 wherein said first and said second conductive surfaces provide an electric signal to said signal translation means when a fluid enters said concentric troughs and contacts said conductive surfaces.

17. The moisture detection pad of claim 15 wherein said apertures are tapered inward from top to bottom and are aligned in a series or concentric rings residing above said concentric troughs.

18. The moisture detection pad of claim 15 wherein said apertures are venture apertures and are aligned in a series or concentric rings residing above said concentric troughs.

19. The moisture detection pad of claim 16 wherein said bottom layer has a system of embedded conductive wires therethrough in electrical communication with said first and second conductive surfaces of said means for moisture signal generation and said signal translation means.

* * * * *